United States Patent [19]

Musser et al.

[11] Patent Number: 4,769,461
[45] Date of Patent: Sep. 6, 1988

[54] QUINOLINYL BENZENE HYDROXAMIC ACIDS AS ANTI-INFLAMMATORY/ANTIALLERGIC AGENTS

[75] Inventors: John H. Musser, Malvern; Dennis M. Kubrak, Drexel Hill, both of Pa.

[73] Assignee: American Home Products Corporation, New York, N.Y.

[21] Appl. No.: 907,933

[22] Filed: Sep. 16, 1986

[51] Int. Cl.$^4$ .................. C07D 215/04; C07D 215/22; C07D 215/36; C07D 215/38
[52] U.S. Cl. ..................................... 546/152; 546/153; 546/155; 546/157; 546/160; 546/161; 546/168; 546/169; 546/176; 546/177; 546/178; 546/179
[58] Field of Search ............... 546/153, 156, 160, 168, 546/169, 152, 161, 177, 155, 157, 176, 178, 179

[56] References Cited

U.S. PATENT DOCUMENTS 3,174,972  3/1965  Allois ................................ 546/161
4,547,509  10/1985 Musser et al. ..................... 546/177

FOREIGN PATENT DOCUMENTS 0161939  5/1985  European Pat. Off. .

*Primary Examiner*—Donald G. Daus
*Assistant Examiner*—Cecilia Shen
*Attorney, Agent, or Firm*—George Tarnowski

[57] ABSTRACT

There are disclosed compounds of the formula

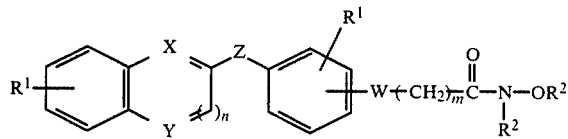

wherein
W represents a covalent bond or

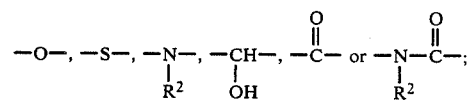

X is N or $CR^2$;
Y is O, S, $NR^2$ or $C(R^2)_2$ when n=0, or N or $CR^2$ when n=1
Z is

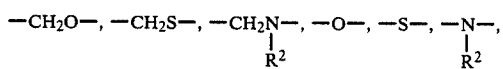

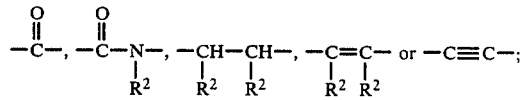

$R^1$ is hydrogen, lower alkyl, trifluoromethyl, nitro, hydroxy, lower alkoxy, mercapto, loweralkylthio or halo;
$R^2$ is hydrogen or lower alkyl;
n is 0-1;
m is 1-6 with the proviso that m is 0-5 when W represents a covalent bond;

and the pharmaceutically acceptable salts thereof, and their use in the treatment of leukotriene-mediated naso-bronchial obstructive airpassageway conditions, such as allergic rhinitis, allergic bronchial asthma and the like, in psoriasis, ulcerative colitis, rheumatoid arthritis as well as in other immediate hypersensitivity reactions.

7 Claims, No Drawings

QUINOLINYL BENZENE HYDROXAMIC ACIDS AS ANTI-INFLAMMATORY/ANTIALLERGIC AGENTS

This invention relates to novel heterocyclic compounds possessing 5-lipoxygenase/cyclooxygenase inhibitory and leukotriene antagonist activity, which are useful as anti-inflammatory and antiallergic agents.

It is known that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. It is now known that prostaglandins arise from the endoperoxides $PGG_2$ and $PGH_2$ by the cyclooxygenase pathway of arachidonic acid metabolism. Other products arising from the endoperoxides in the cyclooxygenase pathway are prostacyclin ($PGI_2$) and the thromboxanes $(Tx)A_2$ and $B_2$. In the normal situation, the vasoconstrictive and platelet aggregating properties of the thromboxanes are balanced by prostacyclin ($PGI_2$). There is now considerable evidence that of the various prostaglandin products of cyclooxygenase metabolism of arachidonic acid, $PGE_2$ plays a major role in the development of inflammatory erythema, edema and pain. It is also known that $PGI_2$ also contributes to these responses. The role of $PGE_2$ in the development of erythema and enhancement of edema explains why cyclooxygenase inhibition agents effectively reduce the redness and swelling associated with most inflammatory conditions [Ferreira and Vane, *Handb. Exp. Pharmacol.*, 50/II, 348-98 (1979)]. $PGE_2$ and $PGI_2$ are also involved in the pain of the inflammatory process; both induce hyperalgesia—sensitization of pain receptors through an edematous reaction or by direct effect—which results in potentiating the pain-producing effects of histamine or bradykinin. The inhibitors of cyclooxygenase, by removing the hyperalgesic cyclooxygenase products, function as analgesics.

In man, cyclooxygenase products have been detected in a number of inflammatory states, including allergic contact eczema, uveitis, arthritis, ulcerative colitis and psoriasis [Higgs et al., in Huskisson, E. C. ed. *Antirheumatic Drugs*, pp. 11-36, Praeger, London. 1983]. Clearly, drugs which exert an effect on the cyclooxygenase pathway of arachidonic acid metabolism are considered to be useful in the treatment of inflammation and inflammatory conditions.

The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $B_4$, $C_4$, $D_4$ and $E_4$. The substance denominated slow-reacting substance of anaphylaxis (SRS-A) has been shown to consist of a mixture of sulfidopeptide leukotrienes, $C_4$, $D_4$ and $E_4$ [see Bach et al., *J. Immun.* 215, 115-118 (1980); *Biochem. Biophys. Res. Commun.* 93, 1121-1126 (1980)].

The significance of these leukotrienes is that a great deal of evidence has been accumulated showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature* 288, 484-486 (1980) and Piper, *Int. Arch. Appl. Immunol.*, 76, suppl. 1, 43 (1985)] which stimulate the release of mucus from airways in vitro [Marom et al., *Am. Rev. Resp. Dis.*, 126, 449 (1982)], are potent vasodilators in skin [see Bisgaard et al, *Prostaglandins*, 23, 797 (1982)], and produce a weal and flare response [Camp et al., *Br. J. Pharmacol.*, 80, 497 (1983)]. The nonpeptide leukotriene, $LTB_4$, is a powerful chemotactic factor for leukocytes [see A. W. Ford-Hutchinson, *J. Roy. Soc. Med.*, 74, 831-833 (1981)], which stimulates cell accumulation and affects vascular smooth muscle [see Bray, *Br. Med. Bull.*, 39, 249 (1983)]. The activity of leukotrienes as mediators of inflammation and hypersensitivity is extensively reviewed in Bailey and Casey, *Ann. Reports Med. Chem.*, 17, 203-217 (1982).

Polymorphonuclear leucocytes (PMN's) are a major source of AA metabolites in the early stages of inflammation and drugs that inhibit leucocyte accumulation in inflamed tissues reduce the concentration of cyclooxygenase products in inflammatory exudates. Thus, cyclooxygenase activity in inflammation may be suppressed through an effect on leucocyte migration. Thus, the suppression of leucocyte migration, which is enhanced by lipoxygenase oxidation products, also contributes to control of the inflammation process.

Accordingly, it is clear that in general inflammatory responses, where PG's are important mediators, dual inhibitors of cyclooxygenase and lipoxygenase must be considered the most useful therapeutic agents. Moreover, the biological activity of the leukotrienes and SRS's, and of lipoxygenase as the enzyme leading to the metabolism of AA to leukotrienes, indicates that a rational approach to drug therapy to prevent, remove or ameliorate the symptoms of allergies, anaphylaxis, asthma and inflammation must focus on either blocking the release of mediators of these conditions or to antagonize their effects. Thus compounds, which inhibit the biological effects of the leukotrienes and SRS's and/or which control the biosynthesis of these substances, as by inhibiting lipoxygenase, are considered to be of value in treating such conditions as allergic bronchial asthma, allergic rhinitis, as well as in other immediate hypersensitivity reactions.

It has now been found that certain novel heterocyclic aryl hydroxamic acid compounds inhibit and/or antagonize products of the cyclooxygenase and lipoxygenase pathways, and so are useful as anti-inflammatory and anti-allergic agents. The present invention provides novel compounds having the following formula:

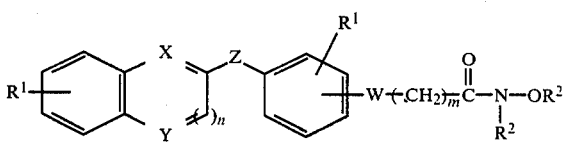

wherein

W represents a covalent bond or

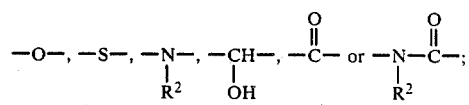

X is N or $CR^2$;

Y is O, S, $NR^2$ or $C(R^2)_2$ when n=0, or N or $CR^2$ when n=1;

Z is $-CH_2O-$, $-CH_2S-$, $-CH_2\underset{R^2}{N}-$, $-O-$, $-S-$, $-\underset{R^2}{N}-$, $-\overset{O}{\underset{}{C}}-$, $-\overset{O}{\underset{}{C}}-\underset{R^2}{N}-$, $-\underset{R^2}{CH}-\underset{R^2}{CH}-$, $-\underset{R^2}{C}=\underset{R^2}{C}-$ or $-C\equiv C-$;

$R^1$ is hydrogen, lower alkyl, trifluoromethyl, nitro, hydroxy, lower alkoxy, mercapto, loweralkylthio or halo;

$R^2$ is hydrogen or lower alkyl;

n is 0–1;

m is 1–6 with the proviso that m is 0–5 when W represents a covalent bond;

and the pharmaceutically acceptable salts thereof.

The terms "lower alkyl" and "lower alkoxy" refer to moieties having 1 to 6 carbon atoms in the carbon chain. The term "halo" refers to fluoro, chloro and bromo.

The compounds of the invention can be prepared in a number of ways. In those instances in which the bridge Z is $-CH_2O-$, the basic intermediate compounds can be prepared by the reaction of an appropriate alkoxyalkanoyl phenyl derivative with the halide of an appropriate benzo-fused heterocyclic derivative in the following representative sequence:

[Reaction scheme showing aryl-CH₂hal + HO-aryl-(CH₂)ₘ-C(O)-OCH₃ → product, with Cs₂CO₃/Acetone]

The intermediates obtained by this sequence can then be further reacted to yield the desired hydroxamic acids and derivatives thereof:

[Reaction scheme: ester → (1) Aq. NaOH (2) R²HNOR² → hydroxamate]

Compounds in which the bridge Z is $$-CH_2S- \text{ and } -CH_2\underset{R^2}{N}-$$

can be prepared in a like manner, starting with intermediates prepared by using the appropriate thiophenol or aniline in place of the phenol derivative. Compounds in which the bridge Z is $$-\overset{O}{\underset{}{C}}-\underset{R^2}{N}-$$

can be prepared by using the appropriate acyl chloride or acyl N-imidazole of the desired benzo-fused heterocyclic and an appropriately N-substituted alkoxyalkanoylaniline.

The starting intermediate compounds for the preparation of compounds in which the linking bridge Z is $$-O-, -S- \text{ or } -\underset{R^2}{N}-$$

can be prepared by the following representative reaction sequence:

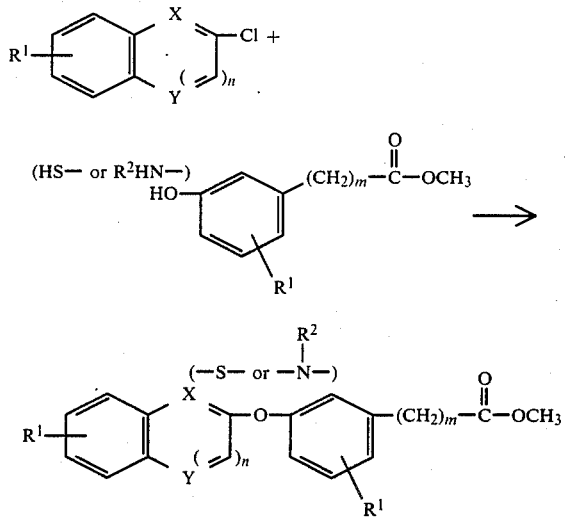

Other compounds within the scope of the invention can be prepared by similar conventional preparative methods using appropriate and readily available starting materials.

The benzo-fused heterocyclic compounds used in the above reaction sequences are either commercially available or can be prepared by methods conventional in the art. Thus, for example, such intermediates as 1-methyl-2-chloromethylbenzimidazole, 2-chloromethylbenzthiazole and 2-chloromethylbenzoxazole can be prepared by the following reaction scheme

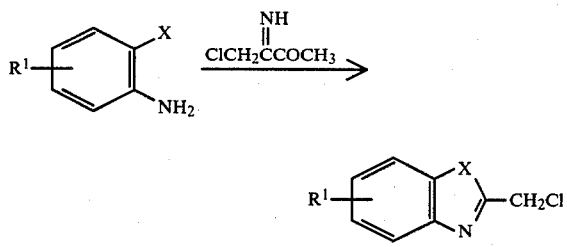

wherein X is O, S or $NHCH_3$. The reaction is preferably carried out at a controlled low temperature in an organic solvent, such as methylene chloride.

Compounds of the invention which contain a basic nitrogen are capable of forming pharmaceutically acceptable salts, including the salts of pharmaceutically acceptable organic and inorganic acids such as hydrochloric, hydrobromic, sulfuric, nitric, phosphoric, methanesulfonic, benzenesulfonic, acetic, citric, fumaric, maleic, succinic and the like.

The compounds of the invention, by virtue of the ability to inhibit the activity of lipoxygenase enzyme and cyclooxygenase enzyme and to antagonize mediators arising from these enzymatic pathways, are useful in the treatment of inflammatory conditions. Accordingly, the compounds are indicated in the treatment of such diseases as rheumatoid arthritis, osteoarthritis, tendinitis, bursitis and similar conditions involving inflammation. Moreover, by virtue of their ability to inhibit the activity of lipoxygenase enzyme and by their ability to antagonize the effect of $LTC_4$, $LTD_4$ and $LTE_4$ which are the constituents of SRS-A, are useful for the inhibition of symptoms induced by these leukotrienes. Accordingly, the compounds are indicated in the prevention and treatment of those disease states in which $LTC_4$, $LTD_4$ and $LTE_4$ are causative factors, for example allergic rhinitis, allergic bronchial asthma and other leukotriene mediated naso-bronchial obstructive air-passageway conditions, as well as in other immediate hypersensitivity reactions, such as allergic conjunctivitis. The compounds are especially valuable in the prevention and treatment of allergic bronchial asthma.

When the compounds of the invention are employed in the treatment of allergic airways disorders and/or as antiinflammatory agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptons presented and the particular subject being treated. Treatment will generally be initiated with small dosages less than the optimum dose of the compound. Thereafter the dosage is increased until the optimum effect under the circumstances is reached. In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The lipoxygenase and cyclooxygenase inhibitory, and luekotriene antagonist effects as well as the antiinflammatory effects of the compounds of the invention may be demonstrated by standard pharmacological procedures, which are described more fully in the examples given hereinafter.

These procedures illustrate the ability of the compounds of the invention to inhibit the polymorphonuclear leukocyte synthesis of the lipoxygenase product 5-HETE, the in vivo ability of the compounds to inhibit bronchospasm induced by endogenous mediators of bronchoconstruction; measure the ability of the compounds to inhibit the synthesis of $PGE_2$; and measure the in vivo activity of the compounds as lipoxygenase and cyclooxygenase inhibitors in the rat carageenan paw edema assay.

The following examples show the preparation and pharmacological testing of compounds within the invention.

EXAMPLE 1

O-methyl-3-[(2-quinolinyl)methoxy]benzeneaceto hydroxamate (A) Methyl-3-[(2-quinolinyl)methoxy]benzeneacetate A mixture of methyl-3-hydroxyphenyl acetate (14.1 g, 85.0 mmol), chloromethylquinoline (15.1 g, 85.0 mmol), cesium carbonate (29.0 g) and acetone (300 ml) is refluxed for 40 hours. The mixture is filtered through Celite and silica gel and the solvent is removed in vacuo to give 25.4 g (97% yield) of oil.

(B) 3-[(2-Quinolinyl)methoxy]benzeneacetic acid

The ester of (A) above (19.5 g, 63.4 mmol) is dissolved in tetrahydrofuran (150 ml) and 1N NaOH (150 ml) is added. The reaction is heated at reflux for 3 hours. The tetrahydrofuran is removed in vacuo and the remaining solution is adjusted to pH 3 using 1N HCl. A precipitate forms which is filtered and dried, giving 17.5 g (94% yield) of product, m.p. 128°–130° C.

(C) O-methyl-3-[(2-quinolinyl)methoxy]benzeneaceto hydroxamate

To a mixture of the acid of (B) above (5.0 g, 17.4 mmol), O-methyl hydroxylamine hydrochloride (1.42 g, 17.4 mmol) and 1-ethyl-3-(3-dimethylaminopropyl)carbodiimide (3.26 g, 17.4 mmol) in tetrahydrofuran (75 ml) is added triethylamine (4.7 ml, 2.2 eq). The reaction is stirred at room temperature overnight. The tetrahydrofuran is removed in vacuo and methylene chloride is added. The mixture is washed with water (2X), dried (MgSO$_4$) and concentrated to an oil. The oil is dissolved in acetone, filtered through Celite and silica gel and concentrated to an oil. The oil is purified by preparative HPLC using ethylacetate/ethanol 95:5 as an eluent. The title compound is isolated giving 1.6 g (29% yield), m.p. 106°–108° C.

EXAMPLE 2

Following the procedure of Example 1, using carbonyldiimidazole in place of 1-ethyl-3-(3-dimethylaminopropyl)carbodiimide as the carboxylic acid activating agent, and using the following starting materials: methyl-3-hydroxyphenyl acetate or methyl-3-hydroxybenzoate, O-methylhydroxylamine or O-benzylhydroxylamine, and 2-chloromethylbenzthiazole or 2-chloromethylbenzoxazole, there are prepared:

(A) O-methyl-3-[(2-quinolinyl)methoxy]benzoic hydroxyamate.

(B) O-benzyl-3-[(2-quinolinyl)methoxy]benzoic hydroxamate.

(C) O-benzyl-3-[(2-quinolinyl)methoxy]benzeneaceto hydroxamate.

(D) O-methyl-3-[1-methyl(2-benzimidazoyl)methoxy]-benzoaceto hydroxamate.

(E) O-methyl-3-[(2-benzthiazoyl)methoxy]benzoaceto hydroxamate.

EXAMPLE 3

3-[(2-Quinolinyl)methoxy]benzeneaceto hydroxamic acid

To a solution of hydroxylamine hydrochloride (4.6 g, 60 mmol) in methanol (25 ml) is added a solution of potassium hydroxide in methanol (25 ml). After cooling, the precipitated potassium chloride is removed by filteration. The ester of Example 1(A) (5.0 g, 16 mmol) is added to the filtrate and stirred for 15 minutes. After cooling, the precipitate is filtered and dried giving the potassium salt of title compound, m.p. 168°–170° C. The potassium salt is treated with acetic acid (25 ml). The resulting solid is filtered, washed with water and dried giving 1.25 g (25% yield) of product, m.p. 195°–197° C.

EXAMPLE 4

Following the procedure of Example 3 and using methyl-3-hydroxybenzoate, there is obtained:

(A) 3-[(2-quinolinyl)methoxy]benzoic hydroxamic acid.

EXAMPLE 5

The compounds 5- and 12-hydroxyeicosatetraenoic acid (5-HETE and 12-HETE) and 5,12-dihydroxyeicosatetraenoic acid (5,12-diHETE) are early arachidonic acid oxidation products in the lipoxygenase cascade, which have been shown to mediate several aspects of inflammatory and allergic response. The assay of this Example measures the ability of the compounds of the invention to inhibit the synthesis of 5-HETE by rat glycogen elicited polymorphonuclear leukocytes.

The assay is carried out as follows:

Peritoneal PMN are obtained from female Wistar rats (150–250 g) that received an i.p. injection of 6% glycogen (10 ml). After 24 hours, rats are killed by $CO_2$ asphyxiation and peritoneal cells are harvested by peritoneal lavage using $Ca^{++}$ and $Mg^{++}$ free Hanks' balanced salt solution (HBSS). The peritoneal exudate is centrifuged at 400 g for 10 minutes. After centrifugation, the lavaged fluid is removed and the cell pellet is resuspended in HBSS containing $Ca^{++}$ and $Mg^{++}$ and 10 mM L-cysteine at a concentration of $2 \times 10^7$ cells/ml. To 1 ml portions of cell suspension, test drugs or vehicle are added and incubated at 37° C. for 10 minutes. Following this preincubation, the calcium ionophore (10 $\mu$M), A23187, is added together with 0.5 $\mu$Ci [$_{14}$C] arachidonic acid and further incubated for 10 minutes. The reaction is stopped by the addition of ice cold water (3 ml) and acidifying to pH 3.5. Lipoxygenase products are then extracted twice into diethyl ether. The pooled ether extracts are evaporated to dryness under nitrogen and the residue is redissolved in a small volume of methanol and spotted on aluminum backed pre-coated thin layer chromatographic plates. The samples are then co-chromatographed with authentic reference 5-HETE in the solvent system-hexane:ether:acetic acid (50:50:3). After chromatography, the areas associated with 5-HETE standard are identified by autoradiography, cut out and quantitated by liquid scintillation.

The compounds of this invention are tested in this assay at a level of 10 $\mu$m. The results are summarized in Table 1, where those compounds having an inhibition of >50% are designated by a "+". Some results are expressed as an $IC_{50}$ value.

TABLE 1

| Compound of Example Number | >50% Inhibitory at 10 $\mu$m | ($IC_{50}$) $\mu$m |
|---|---|---|
| 1 | | 10.5 |
| 2B | + | |

The results show that compounds of this invention have significant activity in inhibiting the synthesis of the arachidonic acid lipoxygenase oxidation product 5-HETE.

EXAMPLE 6

The procedure of Example 5 is also employed for the determination of the ability of the compounds of the invention to inhibit the synthesis of the arachidonic acid cyclooxygenase oxidation product $PGE_2$.

In this assay, the procedure of Example 5 is carried out as described. However, in order to determine cyclooxygenase activity, the samples are cochromatographed with authentic reference $PGE_2$ in the solvent system ethyl acetate:formic acid (80:1) and the upper phase of ethyl acetate:isooctane:acetic acid:water (110:50:20:100). After chromatography, the areas associated with the $PGE_2$ standard are identified by autoradiography, cut out and quantitated by liquid scintillation techniques.

The results are calculated as in Example 5.

Testing compounds of this invention in this assay, the following results are obtained.

TABLE 2

| Compound of Example No. | >50% Inhibition at 10 μm |
|---|---|
| 2B | + |
| 2D | + |

The results show that compounds of this invention have activity in inhibiting the synthesis of the arachidonic acid cyclooxygenase oxidation product $PGE_2$.

EXAMPLE 7

The assay of this Example measures the in vivo ability of the compounds of the invention to inhibit the bronchospasm induced in guinea pigs by the exogenously administered leukotrienes $C_4$ and/or $D_4$.

This assay is carried out as follows:

Male Hartley strain guinea pigs (350–600 g) are anesthetized with pentobarbital sodium (50 mg/kg, i.p.). The jugular vein is cannulated for injection of drugs and the carotid artery for monitoring blood pressure. The trachea is cannulated for artificial ventilation by a miniature Starling pump and for indirect measurement of respiratory volume changes. The animals are then pretreated with succinylcholine (2 mg/kg i.v.) and indomethacin (10 mg/kg i.v. in trizma 8.3 buffer, 9 minutes prior to leukotriene challenge). Submaximal bronchoconstrictor responses are established in control animals by varying the dose-levels of leukotriene. Intravenous dose-levels for $LTC_4$ range from 0.4 to 0.6 μg/kg and for $LTD_4$ the range is from 0.3 to 0.5 μg/kg. The aerosol bronchoprovocation dose for $LTC_4$ is generated from 1.6 μM solution and for $LTD_4$ from a 2.0 μM solution.

Test drugs (dissolved in a solvent such as propylene glycol, polyethylene glycol 400 or saline) are administered either intraduodenally, by aerosol or perorally at 2 or 10 minutes before induction of bronchospasm by administration of either $LTC_4$ or $LTD_4$ at the predetermined dose-levels. Aerosols of soluble drugs or leukotrienes are produced in-line for 10 seconds only by actuation of an ultrasonic nebulizer (Monaghan). Aerosolized drug dosage is expressed in terms of solution concentration and by a fixed aerosol exposure time (approximately 10 seconds). Control animals receive solvent (2 ml/kg i.d. or appropriate aerosol) in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at 1, 3 and 5 minutes are obtained from the recorded charts.

Area under the volume overflow curve (AUC) is estimated, using the overflow values at 1, 3 and 5 minutes, and expressed as a percentage of the maximal overflow AUC (equation 1):

$$\% \max AUC = \frac{3(1 \min) + 4(3 \min) + 2(5 \min)}{10(\max)} \times 100 \quad (1)$$

Drug effects are reported as percent inhibition of % max AUC values obtained from appropriate control animals (equation 2):

$$\% \text{ inhibition} = \frac{\% \max AUC \text{ control} - \% \max AUC \text{ treated}}{\% \max AUC \text{ control}} \times 100 \quad (2)$$

Student's t-test for unpaired data is used to determine statistical significance (p<0.05). $IC_{50}$ values can also be determined by inverse prediction from linear regression lines through points between 10 and 90% inhibition.

The results for compounds of the invention are as follows:

| Compound administered at 10 minutes before induction of bronchospasm | | | |
|---|---|---|---|
| Compound of Example Number | Dose mg/kg | % Inhibition | $IC_{50}$ mg/kg |
| 1 | 25* | 90.6 | 1.8 |
|  | 25** | 86.3 | 5.9 |
| 2A | 25* | 92.8 | 3.16 |
|  | 25** | 72.4 | 13.1 |
| 2B | 25* | 69.4 |  |
| 3 | 25* | 10 |  |
| 4A | 25* | 32.8 |  |

*intraduodenally administered
**perorally administered

The results show that compounds of the invention have significant in vivo activity against $LTD_4$ induced bronchoconstriction.

EXAMPLE 8

The assay of this Example measures the in vivo ability of the compounds of the invention to inhibit the bronchospasm induced in guinea pigs by endogenous mediators of the bronchoconstriction.

The assay is carried out as follows:

Male Hartley strain guinea pigs weighing 250–350 g are sensitized to chicken ovalbumin (OA) (10 mg i.p.) on days 1 and 3 and used starting on day 26. The animals are anesthetized with pentobarbital sodium (50 mg/kg, i.p.), bilateral vagotomy is performed, and the jugular vein is cannulated for injection of drugs and the carotid artery for monitoring blood pressure. The trachea is cannulated for artificial ventilation by miniature Starling pump and for indirect measurement of respiratory volume changes. Succinylcholine (2 mg/kg, i.v.) is administered to arrest spontaneous respiration. A cyclooxygenase inhibitor, indomethacin (10 mg/kg in tris buffer, i.v. at 9 min.) is administered to shunt arachidonic metabolism to lipoxygenase pathways. One minute later, chlorpheniramine (1.0 mg/kg in saline, i.v.) is given to attenuate the histaminic component of anaphylactic bronchoconstriction. Test drugs (dissolved in propylene glycol, polyethylene glycol or saline) are administered either intraduodenally, perorally or by aerosol at 2 or 10 minutes before antigen challenge. Anaphylactic bronchoconstriction is induced by administration by breaths of aerosolized OA (1%) or by intravenous administration of 0.1–0.3 mg/kg OA in saline. Control animals receive solvent (2 ml/kg i.d. or appropriate aerosol) in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at minutes 1, 3 and 5 are obtained from the recorded charts.

Area under the volume overflow curve (AUC) is estimated, using the overflow values at 1, 3 and 5 minutes, and expressed as a percentage of the maximal overflow AUC (equation 1):

$$\% \max AUC = \frac{3(1 \min) + 4(3 \min) + 2(5 \min)}{10(\max)} \times 100 \quad (1)$$

Drug effects are reported as percent inhibition of % max AUC values obtained from appropriate control animals (equation 2):

$$\% \text{ inhibition} = \frac{\% \max AUC \text{ control} - \% \max AUC \text{ treated}}{\% \max AUC \text{ control}} \times 100 \quad (2)$$

Student's t-test for unpaired data is used to determine statistical significance. Dose response curves are generated and $ED_{50}$ doses are interpolated from the regression lines.

Results for compounds of the invention in this assay, using OA for induction of bronchospasm, are given below:

| Compound administered at 10 minutes before intraduodenally administered ovalbumin challenge | | | |
|---|---|---|---|
| Compound of Example Number | Dose mg/kg (Intraduodenal) | % Inhibition of Max AUC | $ED_{50}$ mg/kg |
| 1 | 25 | 56.0 | 7.3 |
|   | 25* | 82.8 | 2.5 |
| 2A | 25 | 76.6 | |
|   | 25* | −1.5 | |

*perorally administered

The results show that the compound tested has significant in vivo activity in inhibiting ovalbumin induced bronchospasm mediated by endogenous products of the lipoxygenase oxidation of arachidonic acid.

EXAMPLE 9

The compounds of the invention are further tested in the rat carrageenan paw edema assay to determine their ability to inhibit the acute inflammatory response.

This assay is carried out as follows:

140–180 gm male Sprague-Dawley rats, in groups of 6 animals are injected subcutaneously in the right paw with 0.1 ml of 1% carrageenan at zero time. Mercury plethysmographic readings (ml) of the paw are made at zero time and 3 hours later. Test compounds are suspended or dissolved in 0.5% methylcellulose and given perorally 1 hour prior to carrageenan administration.

The increase in paw volume (edema in ml.) produced by the carrageenan is measured. Paw edema is calculated (3 hour volume minus zero time volume), and percent inhibition of edema is determined. Unpaired Student's t-test is used to determine statistical significance.

The activity of standard drugs in this assay is as follows:

| Drug | Oral $ED_{50}$ (95% C.L.) mg/kg |
|---|---|
| Indomethacin | 3.7 (0.6, 23.8) |
| Aspirin | 145.4 (33.1, 645.6) |
| Phenylbutazone | 26.2 (2.3, 291.0) |

When tested in this assay, the compounds of the invention gave the following results:

| Compound of Example No. | % Inhibition at 100 mg/kg (peroral) |
|---|---|
| 1 | 50 |
| 2A | 32 |
| 2B | 42 |
| 2C | 37 |
| 2D | 48 |
| 2E | 38 |

The results show that the compounds tested have activity in the rat carrageenan paw edema assay, evidencing an effect on the acute inflammatory response.

What is claimed is:

1. A compound having the formula

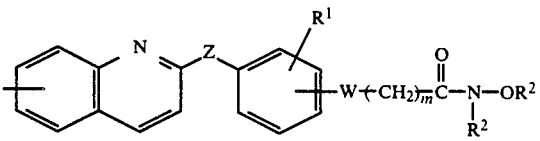

wherein
W represents a covalent bond or

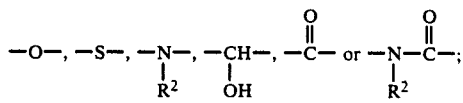

Z is

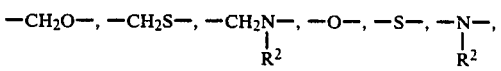

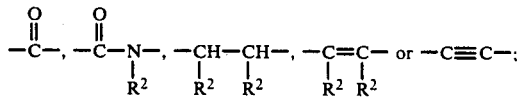

$R^1$ is hydrogen, lower alkyl, trifluoromethyl, nitro, hydroxy, lower alkoxy, mercapto, loweralkylthio or halo;
$R^2$ is hydrogen or lower akyl;
m is 1–6 with the proviso that m is 0–5 when W represents a covalent bond;
and the pharmaceutically acceptable salts thereof.

2. The compound of claim 1, having the name O-methyl-3-[(2-quinolinyl)methoxy]benzeneaceto hydroxamate.

3. The compound of claim 1, having the name O-methyl-3-[(2-quinolinyl)methoxy]benzoic hydroxamate.

4. The compound of claim 1, having the name O-benzyl-3-[(2-quinolinyl)methoxy]benzoic hydroxamate.

5. The compound of claim 1, having the name O-benzyl-3-[(2-quinolinyl)methoxy]benzeneaceto hydroxamate.

6. The compound of claim 1, having the name 3-[(2-quinolinyl)methoxy]benzeneaceto hydroxamic acid.

7. The compound of claim 1, having the name 3-[(2-quinolinyl)methoxy]benzoic hydroxamic acid.

* * * * *